United States Patent
Yuda

(10) Patent No.: US 10,398,162 B2
(45) Date of Patent: Sep. 3, 2019

(54) METHOD FOR MANUFACTURING ALOE EXTRACT, AND ALOE EXTRACT

(71) Applicant: MORINAGA MILK INDUSTRY CO., LTD., Tokyo (JP)

(72) Inventor: Naoki Yuda, Zama (JP)

(73) Assignee: MORINAGA MILK INDUSTRY CO., LTD., Tokyo (JP)

(*) Notice: Subject to any disclaimer, the term of this patent is extended or adjusted under 35 U.S.C. 154(b) by 141 days.

(21) Appl. No.: 15/124,436

(22) PCT Filed: Mar. 19, 2015

(86) PCT No.: PCT/JP2015/058274
§ 371 (c)(1),
(2) Date: Sep. 8, 2016

(87) PCT Pub. No.: WO2015/141787
PCT Pub. Date: Sep. 24, 2015

(65) Prior Publication Data
US 2017/0013868 A1 Jan. 19, 2017

(30) Foreign Application Priority Data
Mar. 20, 2014 (JP) ................. 2014-058002

(51) Int. Cl.
| A61K 36/886 | (2006.01) |
| A23L 33/11 | (2016.01) |
| A61K 8/97 | (2017.01) |
| A61Q 19/00 | (2006.01) |
| A23L 33/105 | (2016.01) |
| A23L 33/21 | (2016.01) |
| A61K 9/16 | (2006.01) |
| A61K 31/575 | (2006.01) |

(52) U.S. Cl.
CPC ............ *A23L 33/11* (2016.08); *A23L 33/105* (2016.08); *A23L 33/21* (2016.08); *A61K 8/97* (2013.01); *A61K 9/16* (2013.01); *A61K 9/1688* (2013.01); *A61K 31/575* (2013.01); *A61K 36/886* (2013.01); *A61Q 19/00* (2013.01); *A23V 2002/00* (2013.01); *A61K 2236/10* (2013.01); *A61K 2236/15* (2013.01); *A61K 2236/17* (2013.01); *A61K 2236/39* (2013.01); *A61K 2236/50* (2013.01); *A61K 2236/51* (2013.01)

(58) Field of Classification Search
None
See application file for complete search history.

(56) References Cited

U.S. PATENT DOCUMENTS

| 6,133,440 A * | 10/2000 | Qiu .................. A61K 31/70 536/123 |
| 2004/0260104 A1 | 12/2004 | Sicre et al. |
| 2011/0038906 A1 | 2/2011 | Yagi |
| 2013/0079314 A1 | 3/2013 | Tanaka et al. |

FOREIGN PATENT DOCUMENTS

| JP | 4-149134 A | 5/1992 |
| JP | 2000-093110 A | 4/2000 |
| JP | 2002-542161 A | 12/2002 |
| JP | 2008-500023 A | 1/2008 |
| WO | WO 99/19505 A1 | 4/1999 |
| WO | WO 2007/060911 A1 | 5/2007 |

OTHER PUBLICATIONS

Moon et al. (1999) Angiogenesis, 3: 117-123. (Year: 1999).*
Afzal et al. (1991) Planta Med. 57: 38-40. (Year: 1991).*
Choi et al. (2003) Seminars in Integrative Medicine, vol. 1, No. 1 pp. 53-62. (Year: 2003).*
International Search Report (PCT/ISA/210) issued in PCT/JP2015/058274, dated Jun. 23, 2015.
Pugh et al., "Characterization of Aloeride, a New High-Molecular-Weight Polysaccharide from Aloe vera with Potent Immunostimulatory Activity", J. Agric. Food Chem., vol. 49, No. 2, 2001, pp. 1030-1034.
Rodríguez et al., "Aloe vera as a Functional Ingredient in Foods", Critical Reviews in Food Science and Nutrition, vol. 50, 2010, pp. 305-326.
Tanaka et al., "Identification of Five Phytosterols from Aloe Vera Gel as Anti-diabetic Compounds", Biol. Pharm. Bull., vol. 29, No. 7, Jul. 2006, pp. 1418-1422.
Written Opinion (PCT/ISA/237) issued in PCT/JP2015/058274, dated Jun. 23, 2015.

* cited by examiner

Primary Examiner — Russell G Fiebig
(74) Attorney, Agent, or Firm — Birch, Stewart, Kolasch & Birch, LLP

(57) ABSTRACT

A major object of the present technology is to provide a technology for obtaining an aloe extract which has an excellent processability into foods and contains sufficient amounts of β-sitosterol and aloe-derived dietary fibers as functional components. The present technology provides a method for manufacturing an aloe extract containing β-sitosterol, phospholipids, and dietary fibers which involves carrying out: a homogenization step for homogenizing an aloe mesophyll solution; an enzymatic degradation step for adding a polysaccharide-degrading enzyme to the homogenized aloe mesophyll solution and degrading polysaccharides contained in the aforementioned homogenized aloe mesophyll solution; and a membrane filtration step for membrane-filtering the enzyme-degraded aloe mesophyll solution with a microfiltration membrane or an ultrafiltration membrane and recovering the retentate fraction as an aloe extract.

8 Claims, 4 Drawing Sheets

[Fig. 1]
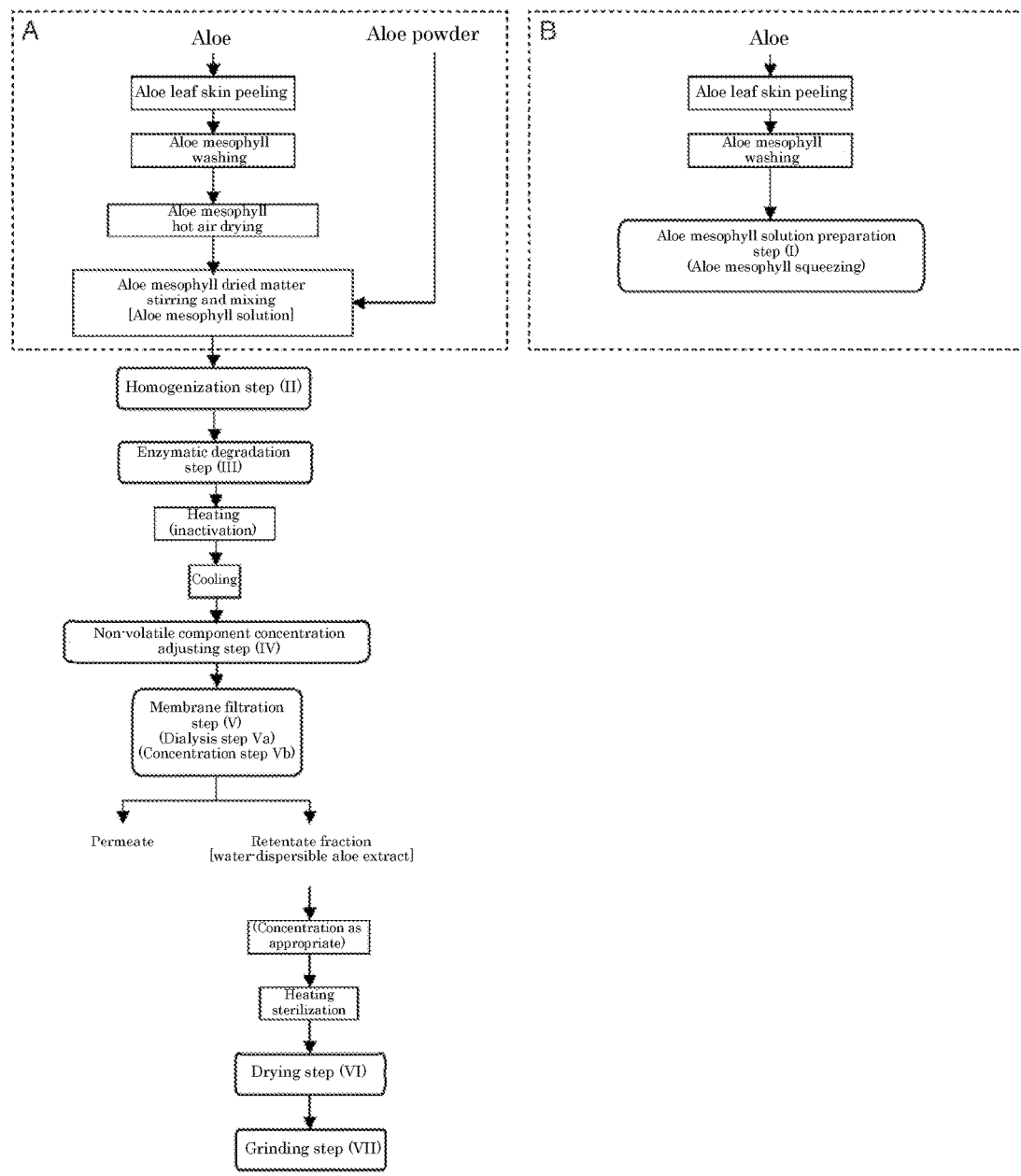

[Fig. 2]
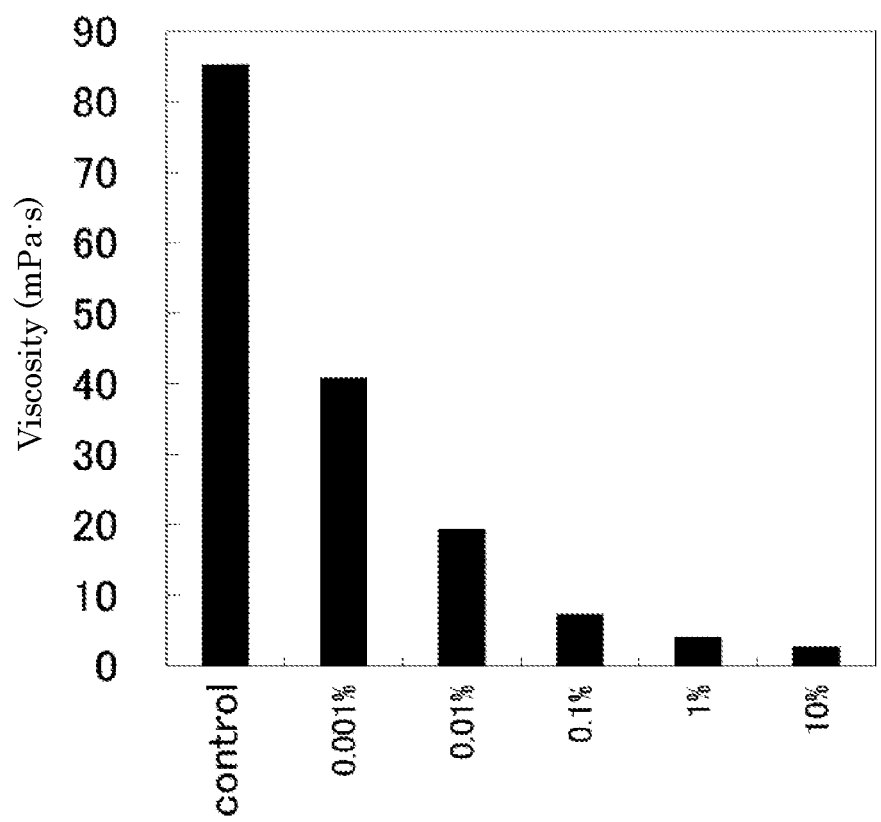

[Fig. 3]
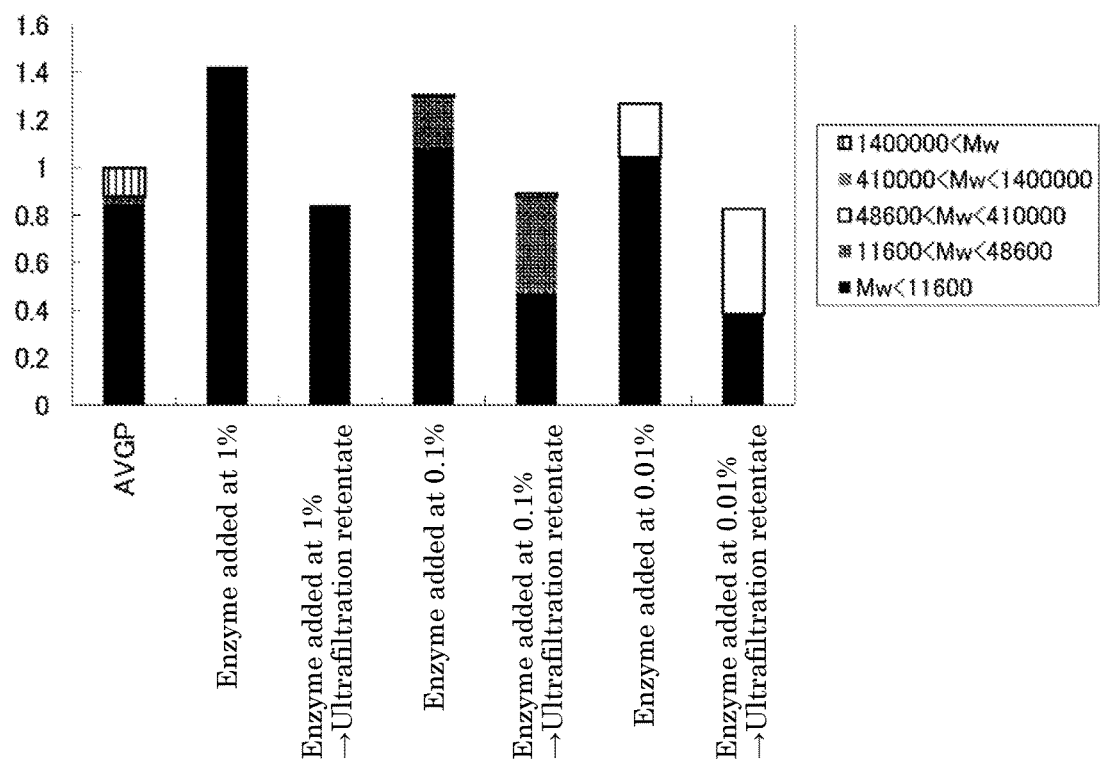

[Fig. 4]
 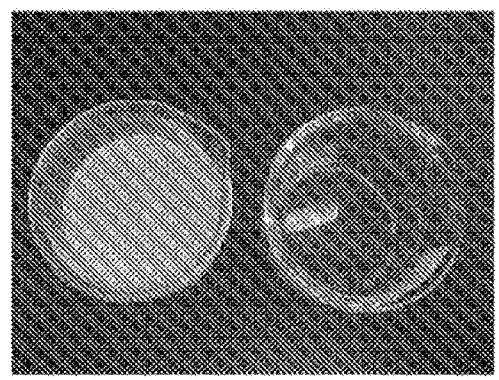
Sample 6 Supercritical carbon dioxide extract    Sample 6 Supercritical carbon dioxide extract
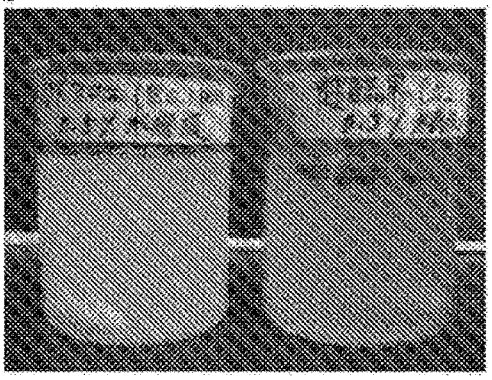 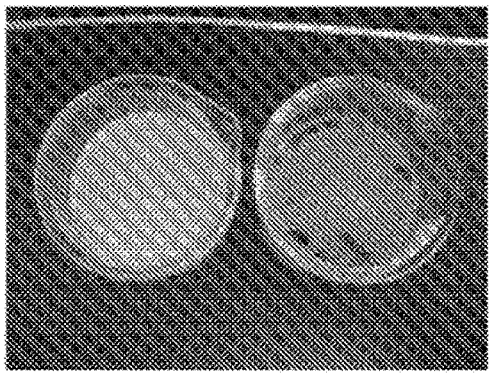
Sample 6 Supercritical carbon dioxide extract    Sample 6 Supercritical carbon dioxide extract

METHOD FOR MANUFACTURING ALOE EXTRACT, AND ALOE EXTRACT

TECHNICAL FIELD

The present invention relates to a method for manufacturing aloe extract. More specifically, it relates to a method for manufacturing aloe extract which exhibits an excellent processability into foods, contains sufficient amounts of functional components, and exhibits a satisfactory water dispersibility and a satisfactorily water-dispersible aloe extract manufactured by the manufacturing method as well as a method for manufacturing a satisfactorily water-dispersible aloe extract powder.

BACKGROUND ART

Aloe is a generic name of succulent plants belonging to Aloaceae of Liliales, and it is believed that there are 300 or more varieties. Among those, aloe vera has been said to keep the doctor away since a long time ago and has been used externally and internally as a folk remedy for a long time. Recently, functions possessed by aloe became attractive and are investigated for utilization in functional foods, supplements, medicaments, cosmetics, and the like. For example, dietary fibers are contained as major components in the aloe, and functional foods, supplements, medicaments, cosmetics, and the like which utilize this dietary fiber are investigated.

Although the dietary fibers contained in the aloe have not been known entirely, there are known water-soluble dietary fibers, namely, glucomannan and acemannan (Non-patent Document 1). In addition, Non-patent Document 2, for example, discloses that the dietary fibers contained in the aloe have physiological effects such as an immune stimulating effect.

It is also known that the aloe contains a trace amount of sterols. The trace amount of the sterol contained in the aloe was found to have an anti-diabetic effect (Non-patent Document 3). These phytosterols are known to exist focally as being surrounded by lipid bilayer membrane of a cell membrane.

Various technologies are being developed for manufacturing an extract in which the aforementioned functional components contained in the aloe are concentrated or for purifying the functional components. For example, Patent Document 1 discloses a method for obtaining a bitterness-free aloe extract by treating an aloe extract with a pectinase followed by adding an activated charcoal thereby allowing bitter components to be adsorbed. Patent Document 2 also discloses a method for manufacturing an aloe solution which has a reduced amount of a substance causing bitterness or astringency such as oxalic acid, is highly transparent, undergoes no precipitation, has a low viscosity, and is rich in mucopolysaccharides by treating an aloe mesophyll-derived solution with a pectinase followed by adding a calcium agent and filtration. Nevertheless, these methods are problematic because they allow the insoluble dietary fibers which are functional components of the aloe to be removed.

Patent Document 3 discloses a method for obtaining an aloe-derived polysaccharide concentrate by heating an aloe juice, adding a cellulase, conducting an incubation with stirring, inactivating the enzyme by heating, cooling, and then conducting filtration through charcoal, filter paper, and kieselguhr. As an alternative method for obtaining a similar composition, a method is disclosed in which an aloe gel is stirred and filtered through a filter paper, the resultant filtrate is decomposed enzymatically by adding a cellulase, the resultant solution is subjected to an ultrafiltration membrane to accomplish dialysis, and a retentate is obtained. Nevertheless, these methods are problematic because they allow the insoluble dietary fibers and phytosterols which are functional components of the aloe to be removed.

Patent Document 4 discloses a method for manufacturing an aloe vera extract containing phytosterols contained in a naturally-occurring aloe vera by a supercritical extraction. Patent Document 5 also discloses a method for recovering a phytosterol from a rapeseed oil and a soybean oil using methanol and a method for isolating a phytosterol by immersing a crude phytosterol in an organic solvent followed by separating the organic solvent off. Although these methods can concentrate the phytosterols contained in the aloe, they are problematic because they allow the dietary fibers which are functional components of the aloe to be removed. It is also problematic that a phytosterol, once isolated, becomes a waxy solid substance at ambient temperature or lower which is hardly miscible with water and difficult to be added to a food. Furthermore, an organic solvent is also problematic since it poses a substantial burden to the operator who uses it as described in Cited Document 5.

As another method, a method for manufacturing an aloe powder and an aloe juice having an aloin content of 50 ppm or less and a molecular weight of a contained polysaccharide of 400,000 dalton or more by immersing an aloe vera gel in water or an extremely dilute aqueous solution is disclosed in Patent Document 6. Nevertheless, this method is problematic since it allows, upon the aforementioned immersion, the water soluble dietary fibers to be eluted together, resulting in a loss of functional components of the aloe mesophyll.

CITATION LIST

Patent Literatures

[Patent Document 1] JP-A No. H04-149134
[Patent Document 2] JP-A No. 2000-93110
[Patent Document 3] WO No. 1999/019505
[Patent Document 4] WO No. 2007/060911
[Patent Document 5] JP-T No. 2002-542161
[Patent Document 6] JP-T No. 2008-500023

Non-Patent Literatures

[Non-Patent Document 1] Crit. Rev. in Food Sci. Nutr., Volume 50, Issue 4, 2010, 305-326
[Non-Patent Document 2] J. Agric. Food Chem., 2001, 49, 1030-103
[Non-Patent Document 3] Biol. Pharm. Bull., 2006, 29, 1418-1422.

SUMMARY OF INVENTION

Technical Problem

As described above, various developments have been ongoing for technologies for manufacturing an extract having a concentrate of functional components contained in aloe and for purifying the functional components. Nevertheless, it is difficult, by conventional technologies, to accomplish concentration while retaining sufficient amounts of various functional components contained in aloe such as both of phytosterols and dietary fibers. It is also problematic that an individually purified functional component has a poor processability into foods.

Accordingly, a major object of the present technology is to provide a technology for obtaining a satisfactorily water-dispersible aloe extract which has an excellent processability into foods and contains sufficient amounts of β-sitosterol and aloe-derived dietary fibers as functional components.

Solution to Problem

The inventors made an intensive study with regard to methods for manufacturing aloe extracts for solving the aforementioned problems and finally established this technology by focusing on the site where β-sitosterol is localized in the aloe mesophyll and taking an approach which is different from conventional concentration and purification technologies. More specifically, conventional methods were mostly focusing on the technologies which allow the functional components to be contained at high purities and in large amounts upon producing an extract having concentrated functional components and upon purifying the functional components. On the contrary, the present technology took an approach which is different from conventional concentration and purification technologies and it was discovered that the aforementioned problems can be solved by concentrating the functional component (β-sitosterol) in its naturally-occurring condition, thereby establishing the present technology.

Thus, the present technology provides, firstly, a method for manufacturing an aloe extract containing β-sitosterol, phospholipids, and dietary fibers which involves carrying out:

a homogenization step for homogenizing an aloe mesophyll solution;

an enzymatic degradation step for adding a polysaccharide-degrading enzyme to the homogenized aloe mesophyll solution and degrading polysaccharides contained in the aforementioned homogenized aloe mesophyll solution; and, a membrane filtration step for membrane-filtering the enzyme-degraded aloe mesophyll solution with a microfiltration membrane or an ultrafiltration membrane and recovering the retentate fraction as an aloe extract.

The aloe extract manufactured by the manufacturing method according to this technology is characterized in that the β-sitosterol exists, as in the natural environment, focally as being surrounded by lipid bilayer membrane of a cell membrane whose major components are phospholipids.

In the aforementioned enzymatic degradation step in the manufacturing method according to the present technology, it is also possible to add 0.01 to 1.0% by mass of the aforementioned polysaccharide-degrading enzyme based on aloe mesophyll non-volatile components contained in the aforementioned homogenized aloe mesophyll solution thereby degrading polysaccharides contained in the aloe mesophyll solution.

In the manufacturing method according to the present technology, it is possible to use hemicellulase as the aforementioned polysaccharide-degrading enzyme.

In the aforementioned membrane filtration step in the manufacturing method according to the present technology, it is also possible to membrane-filter the aforementioned enzyme-degraded aloe mesophyll solution with a microfiltration membrane thereby recovering the retentate fraction as an aloe extract.

In the manufacturing method according to the present technology, it is also possible to further carry out, before the aforementioned homogenization step, an aloe mesophyll solution preparation step for recovering, as the aforementioned aloe mesophyll solution, a squeezed liquid obtained by squeezing the aloe mesophyll.

In the manufacturing method according to the present technology, it is also possible to further carry out, after the aforementioned enzymatic degradation but before the aforementioned membrane filtration step, a non-volatile component concentration adjusting step for adjusting the concentration of the aloe mesophyll non-volatile components in the enzyme-degraded aloe mesophyll solution.

Also in the manufacturing method according to the present technology, it is also possible to carry out a drying step for drying the aforementioned aloe extract which is then recovered as a dried matter.

In addition, in the manufacturing method according to the present technology, it is also possible to carry out, after the aforementioned drying step, a grinding step for grinding the aforementioned dried matter.

The present technology provides, secondly, the aforementioned aloe extract wherein the aforementioned aloe extract contains, based on the solid content of the aloe extract, 2.5 mg/g or more and 7.5 mg/g or less of β-sitosterol and 400 mg/g or more and 900 mg/g or less of dietary fibers.

The aloe extract according to the present technology can be manufactured using the manufacturing method according to the aforementioned present technology.

The median size of the particles contained in the aloe extract according to the present technology is 100 μm or less and the 90% particle size is 200 μm or less.

Advantageous Effects of Invention

By using the manufacturing method according to the present technology, it is possible to provide a satisfactorily water-dispersible aloe extract which has an excellent processability into foods and contains sufficient amounts of β-sitosterol and aloe-derived dietary fibers as functional components. The advantageous effects described here are not necessarily limited and any of the advantageous effects described in the present technology may be contemplated.

BRIEF DESCRIPTION OF DRAWINGS

FIG. 1 is a flowchart of the method for manufacturing an aloe extract according to the present technology. In the flowchart of FIG. 1, the flow in Part A surrounded by a dotted line indicates that it can be replaced by the flow in Part B surrounded similarly by a dotted line.

FIG. 2 is a drawing-substituting graph indicating the viscosity measurement results in Experimental Example 2.

FIG. 3 is a drawing-substituting graph indicating the results of the calculation of relative values of water-soluble polysaccharides contained in respective samples in Experimental Example 3.

FIG. 4 is a drawing-substituting photograph indicating the water dispersibility in Experimental Example 5.

DESCRIPTION OF EMBODIMENTS

Hereinafter, embodiments for carrying out the present technology are described in detail. It should be understood that the embodiments described below show only a part of the representative embodiments of the present technology, which does not serve to restrict the present technology to the embodiments described below.

<Method for Manufacturing Aloe Extract>

FIG. 1 is a flowchart of the method for manufacturing an aloe extract according to the present technology. In the present technology, "aloe extract" is referred to also as "satisfactorily water-dispersible aloe extract", and in such a case the "aloe extract" and the "satisfactorily water-dispersible aloe extract" are regarded to have an almost identical meaning.

Also in this technology, the "aloe extract" includes all materials extracted from an aloe, and its final form is not limited particularly. For example, the "aloe extract" of the present technology is not only a material in a liquid state but also a material which has been processed into a solid state (dried matter and its powder) or a semi-solid state by drying. Hereinafter, the "aloe extract" of the present technology includes all forms encompassing the liquid state, the solid state (dried matter and its powder), the semi-solid state, and the like, unless otherwise specified. It should be understood that when the relevant aloe extract specifically means a dried matter obtained by drying an aloe extract in a liquid state then it may be referred to as "aloe-extracted dried matter".

The method for manufacturing a satisfactorily water-dispersible aloe extract according to the present technology is a method which uses an aloe mesophyll as a raw material and carries out a homogenization step (II), an enzymatic degradation step (III), and a membrane filtration step (V). When the final form of the satisfactorily water-dispersible aloe extract according to the present technology is a dried matter, it is possible to carry out a drying step (VI) in addition to the aforementioned enzymatic degradation step (III) and the aforementioned membrane filtration step (V). Furthermore, it is possible, if necessary, to carry out an aloe mesophyll solution preparation step (I), a non-volatile component concentration adjusting step (IV), grinding step (VII), and the like. Hereinafter, raw materials and individual steps are described in detail. While the individual steps are described in chronological order, all steps are not necessarily essential.

(1) Raw Materials

The aloe used as a raw material in this technology is a generic name of succulent plants belonging Liliales/Aloaceae/Aloe, and 300 or more varieties are known. Aloe vera and Aloe arborescens inhabit Japan predominantly. The raw materials capable of being employed in the manufacturing method according to the present technology are not limited particularly as long as they are succulent plants belonging to the aforementioned Aloe, and any one or more known aloes can be selected and employed. In the present technology, it is preferable to use aloe vera because it has a substantial history of being ingested and can be obtained as a raw material relatively easily.

In the manufacturing method according to the present technology, an aloe mesophyll is employed. As a mesophyll, an aloe mesophyll obtained by peeling the skin of the raw leaf of an aloe and taking the mesophyll part out can be used, or an aloe mesophyll obtained by chopping an raw leaf of an aloe by using a cutter and the like can be used. It is also possible to use one obtained by heating such an aloe mesophyll. It is further possible if necessary to use a mesophyll which was washed. In the present technology, it is preferable to use, as an aloe mesophyll, a mesophyll which contains no skin of the aloe, since the aloe skin and a viscous material adhering to the circumference of the aloe mesophyll contain a pharmacologically active substance such as anthraquinone and exhibit a substantial bitterness.

The washing of the aloe mesophyll is conducted preferably by rinsing the aloe mesophyll thoroughly with water, followed by heat treatment in a hot water and then completely removing the viscous material in the circumference of the mesophyll. The aforementioned heat treatment is conducted preferably under a heating condition employing a hot water at 95° C. or higher for a period of 2 minutes or longer.

(2) Aloe Mesophyll Solution Preparation Step (I)

The aloe mesophyll solution preparation step (I) is a step, before the homogenization step described below, for recovering, as the aforementioned aloe mesophyll solution, a squeezed liquid obtained by squeezing the aloe mesophyll. In the manufacturing method according to the present technology, this aloe mesophyll solution preparation step (I) may not be carried out, for example, if the aforementioned aloe mesophyll solution is prepared using a commercially available dried matter obtained by drying an aloe mesophyll.

While the solid amount of the aloe mesophyll solution recovered in the aloe mesophyll solution preparation step (I) is not limited particularly, it is preferable that an aloe mesophyll solution whose solid amount has been adjusted at 1 to 5% is recovered as a squeezed liquid in view of the amount of the liquid to be processed and easier handling in the later enzymatic degradation step (III).

(3) Homogenization Step (II)

In the manufacturing method according to the present technology, a homogenization step (II) for homogenizing the aloe mesophyll solution is carried out. The homogenization step (II) is a step for exerting a shear force to particles in the aloe mesophyll solution to effect conversion into microparticles thereby improving the water dispersibility.

In the homogenization step (II), the aloe mesophyll solution is employed as a raw material. The aloe mesophyll solution used herein is a solution in which the solid content (non-volatile components) derived from the aforementioned aloe mesophyll is dispersed in water. This aloe mesophyll solution may be a solution obtained by drying the aloe mesophyll and then dispersing the dried matter again in water, or a squeezed liquid obtained by squeezing the aloe mesophyll in the aforementioned aloe mesophyll solution preparation step (I). In the case where the aloe mesophyll is dried, it is also possible to use one which was dried by a known method such as freeze drying, hot air drying, and the like. It is also possible to use one whose water dispersibility was improved by grinding the aloe mesophyll dried matter using a grinder such as a mill. When conducting grinding of the aloe mesophyll dried matter, the water dispersibility is improved particularly by conducting the grinding to a mean particle size of the ground aloe mesophyll dried matter of as small as 30 µm or less. While the aloe mesophyll-derived solid amount of the aloe mesophyll solution is not limited particularly, a solid amount of 1 to 5% by mass is preferable when aiming at easier handling in the homogenization step (II).

The means for the homogenization process in the homogenization step (II) is not limited particularly as long as it is a means by which a particle in the aloe mesophyll solution can be sheared physically, and any one or more of known homogenization means can be selected and employed. For example, a means for homogenizing the particles by passing the aloe mesophyll solution forcibly through a channel having pores or a means for homogenizing the particles by rotating a stirring blade such as one having a shape of propeller and the like in a chamber can be employed. As an instruments having such a means, a known instrument having a shearing ability such as a high pressure homogenizer, homomixer, and high speed flow mixer can be employed for accomplishing homogenization.

While the homogenization condition of the aloe mesophyll solution is not limited particularly, when using a high pressure homogenizer, for example, the aloe mesophyll solution can be subjected to the homogenization process at a uniform pressure of total pressure 10 to 80 MPa. Also when using a homomixer (for example, trade name "Homomixer MARK Model II 2.5 (manufactured by PRIMIX Corporation) and the like), the homogenization process of the aloe mesophyll solution can be accomplished by stirring for 15 to 45 minutes at a rotation speed of 10000 rpm to 20000 rpm.

The aloe mesophyll solution recovered in the homogenization step (II) preferably has the particle size distribution of the particles in the homogenized aloe mesophyll solution characterized by a median size of 100 μm or less and a 90% particle size of 200 μm or less. Any aloe mesophyll solution containing the particles satisfying such a particle size distribution (hereinafter also referred to as "dispersed particles" in the present technology) has satisfactory water dispersibility. As the aforementioned particle size distribution, the value obtained by measurement using known instruments such as a laser diffraction/scattering particle size distribution measuring device (for example LA-500; manufactured by Horiba Ltd.) can be used.

While the solid amount of the aloe mesophyll solution recovered in the homogenization step (II) is not limited particularly, it is preferable to recover the solution as an aloe mesophyll solution whose solid amount has been adjusted at 1 to 5% in view of the amount of the liquid to be processed and easier handling in the later enzymatic degradation step (III).

(4) Enzymatic Degradation Step (III)

The enzymatic degradation step (III) is a step for adding a polysaccharide-degrading enzyme to the homogenized aloe mesophyll solution and degrading polysaccharides contained in the aforementioned aloe mesophyll solution. An aloe mesophyll solution used in the enzymatic degradation step (III) may be one obtained by homogenizing the squeezed fluid obtained by squeezing the aloe mesophyll as it is by conducting the aforementioned aloe mesophyll solution preparation step (I) or one obtained by homogenizing a solution which was obtained by drying the aloe mesophyll and then dispersing the dried matter again in water. In the case where the aloe mesophyll is dried, it is also possible to use one which was dried by a known method such as freeze drying, hot air drying, and the like. It is also possible to use one whose water dispersibility was improved by grinding the aloe mesophyll dried matter using a grinder such as a mill.

While the solid amount of the homogenized aloe mesophyll solution used in the enzymatic degradation step (III) is not limited particularly, it is preferable to effect dispersion in water so that the solid amount becomes 1 to 5% in view of the amount of the liquid to be processed and easier handling. While the pH of the aloe mesophyll solution employed in the enzymatic degradation step (III) is not limited particularly, the pH may be adjusted, if necessary, at 3 to 10 as appropriate.

The enzymatic degradation step (III) is carried out for degrading the polysaccharides in the aloe mesophyll thereby reducing the viscosity of the aloe mesophyll solution while maintaining the state where the β-sitosterol contained in the aloe mesophyll and the phospholipids which are predominant in the cell membrane form a lipid bilayer membrane (water dispersibility). A reduction in the viscosity is effective also in improving the efficiency of the filtration carried out in the subsequent membrane filtration step (V) (fouling is reduced). As a result of carrying out the enzymatic degradation step (III), the resultant satisfactorily water-dispersible aloe-extracted dried matter subsequently exerts effect also in improving the flowability of a ground powder.

The type of the polysaccharide-degrading enzyme which can be employed in the enzymatic degradation step (III) is not limited particularly as long as the enzyme is a cellulose-degrading enzyme, and any one or more of known polysaccharide-degrading enzyme can be selected and employed. Those which can be exemplified are polysaccharide-degrading enzymes such as hemicellulase, cellulase, and pectinase, as well as proteases having a cellulase activity and a hemicellulase activity as their auxiliary activities. Typical enzyme formulations may for example be polysaccharide-degrading enzymes such as hemicellulase "AMANO" 90, cellulase A "AMANO" 3, cellulase T "AMANO" 4, pectinase G "AMANO", pectinase PL "AMANO" (all manufactured by Amano Enzyme Inc.), cellulase "ONOZUKA" 3S, cellulase Y-NC, pectinase SS, pectinase 3S, and pectinase HL (all manufactured by Yakult Pharmaceutical Industry Co., Ltd.), as well as protease A "AMANO" SD(manufactured by Amano Enzyme Inc.) having a cellulase activity and a hemicellulase activity as its auxiliary activities. Among these, it is especially preferable in this technology to select a hemicellulase capable of efficiently reducing the viscosity.

The amount of the polysaccharide-degrading enzyme employed in the enzymatic degradation step (III) is not limited particularly, and any amount can be employed depending on the amount of the aloe mesophyll employed, the condition of the membrane filtration step (V) described below, the intended use of the produced satisfactorily water-dispersible aloe extract, and the like. In the present technology, it is preferable especially to use 0.01% by mass or more and 1.0% by mass or less of the polysaccharide-degrading enzyme based on the solid amount of the aloe mesophyll. By using 0.01% by mass or more of the polysaccharide-degrading enzyme, the filtration efficiency in the membrane filtration step can be improved, and the flowability of the powder obtained by grinding the produced satisfactorily water dispersible aloe-extracted dried matter can also be improved (angle of repose can be reduced). Also as shown in Experimental Example described below, an amount of 1.0% by mass or more can not be expected to give a correspondingly substantial reduction in the viscosity and it is poorly necessary to reduce the viscosity to a level equal to or less than the viscosity achievable with 1.0% by mass, and therefore the upper limit of 1.0% by mass or less serves for a reduced expense. In the case of an enzyme formulation containing dextrin and the like, the calculation should be made using the amount of the enzyme contained.

The reaction condition in the enzymatic degradation step (III) is not limited particularly, and any condition can be used depending on the type of the enzyme employed, the amount of the aloe mesophyll, and the like. In the present technology, for example, the incubation can be conducted for 0.25 to 3 hours with stirring at a temperature of 25 to 70° C. An incubation period as short as possible is preferable because a prolonged incubation poses an increased risk of bacterial growth. The endpoint of the incubation can be determined based on the viscosity, and the enzymatic degradation can be terminated at the time when a vibration-type viscometer (for example, VIBRO VISCOMETER CJV5000; manufactured by A&D Company, Limited) indicates a value within 10 mPa·s to 20 mPa·s. In an exemplary viscosity measurement method, this vibration-type viscometer is employed to measure the viscosity (mPa·s) at room temperature 60 seconds after the start of vibration of a sample in a volume of 80 mL which was placed in a 100-mL beaker.

It is preferable to start heating immediately after termination of the enzymatic degradation thereby inactivating the enzyme. The heating serves also to sterilize the enzymatically degraded liquid of the aloe mesophyll. The heating condition here is not limited particularly, and any condition can be employed depending on the type of the enzyme employed. In the present technology, for example, the inactivation can be accomplished by heating at 90° C. for 10 minutes or longer. During the inactivation by heating, it is preferable to avoid an excessive heating because such an excessive heating may allow the polysaccharide to be degraded.

It is preferable to start cooling immediately after termination of the inactivation by heating thereby preventing bacterial contamination or polysaccharide degradation. The cooling condition here is not limited particularly, and any condition can be employed depending on the type of the enzyme employed. In the present technology, for example, cooling to 10° C. or below is possible.

(5) Non-volatile Component Concentration Adjusting Step (IV)

The non-volatile component concentration adjusting step (IV) is a step, after completing the enzymatic degradation step (III) but before the membrane filtration step (V), for adjusting the concentration of the aloe mesophyll non-volatile components in the aloe mesophyll solution. In the manufacturing method according to the present technology, it is preferable to carry out this non-volatile component concentration adjusting step (IV) for the purpose of improving the efficiency of the membrane filtration step (V) which is carried out later.

In the non-volatile component concentration adjusting step (IV), the typical concentration of the aloe mesophyll non-volatile components in the aloe mesophyll solution is not limited particularly, and preferably 2% by mass or less when aiming at an improvement in the efficiency of the membrane filtration step (V) carried out later.

(6) Membrane Filtration Step (V)

The membrane filtration step (V) is a step for membrane-filtering the aloe mesophyll solution which has completed the aforementioned enzymatic degradation step (III) and recovering the retentate fraction as a satisfactorily water-dispersible aloe extract. The membrane filtration is conducted by using a microfiltration membrane or an ultrafiltration membrane. The membrane filtration step (V) is carried out to concentrate the dispersed particles containing β-sitosterol, phospholipids, and dietary fibers into a retentate fraction using the aloe mesophyll enzymatically-degraded liquid obtained in the aforementioned enzymatic degradation step (III). At the same time, it is carried out for recovering organic acid salts and mineral salts contained in the aloe mesophyll solution into the permeate side of the membrane filtration. Separating the organic acid salts and mineral salts is effective in improving the flavor of the satisfactorily water-dispersible aloe extract recovered into the retentate side (reduction in acidic taste as a result of reduction in organic acid salts) and in improving the flowability of the powder obtained by grinding the produced satisfactorily water dispersible aloe-extracted dried matter (reduction in hygroscopicity as a result of reduction in mineral salts).

In the membrane filtration step (V), either a microfiltration membrane or an ultrafiltration membrane can be selected and used in filtration depending on the purpose. For example, when aiming at efficiently concentrating the dispersed particle containing β-sitosterol, phospholipids, and dietary fibers, it is preferable to use the microfiltration membrane. When aiming at an improved flavor of the satisfactorily water-dispersible aloe extract and an improved flowability of the powder obtained by grinding the produced satisfactorily water-dispersible aloe-extracted dried matter, it is preferable to use the ultrafiltration membrane.

When using a microfiltration membrane, the membrane pore size is not limited particularly, and any design may be allowed depending on the particle size of the dispersed particles and the like. In this technology, it is especially preferred to use a microfiltration membrane having a pore size of 0.25 μm or less. By using a microfiltration membrane having a pore size of 0.25 μm or less, the dispersed particles containing β-sitosterol, phospholipids, and dietary fibers can be concentrated more efficiently.

When using an ultrafiltration membrane, the molecular weight cut-off is not limited particularly, and any design may be allowed depending on the size of the dispersed particles and the like. In this technology, it is especially preferred to use an ultrafiltration membrane having a molecular weight cut-off of 6000 Da or more and 10000 Da or less. By using an ultrafiltration membrane having a molecular weight cut-off of 6000 Da or more, it is possible to recover organic acid salts and mineral salts into the permeate side while preventing the membrane fouling. In addition, by using an ultrafiltration membrane having a molecular weight cut-off of 10000 Da or less, it is possible to maintain the yield of the dispersed particles containing β-sitosterol, phospholipids, and dietary fibers at a sufficient level.

The membrane employed typically in the membrane filtration step (V) may for example be a hollow fiber membrane, spiral membrane, flat membrane, and the like. When aiming at prevention of membrane fouling or improved concentration magnification, it is preferred to use a hollow fiber membrane or a flat membrane. The name of the typical product which can be employed may for example be Microza (manufactured by Asahi Kasei Chemicals Corporation) or LabStak (manufactured by Alfa Laval K.K.).

In the membrane filtration step (V), the typical procedure is not limited particularly and any design may be allowed as long as the dispersed particles containing β-sitosterol, phospholipids, and dietary fibers can be concentrated into the retentate fraction and organic acid salts and mineral salts contained in the aloe mesophyll solution can be recovered into the permeate side of the membrane filtration. In the present technology, it is particularly preferred to carry out 2 steps, namely, a dialysis step (Va) and a concentration step (Vb) in the membrane filtration step (V).

In the dialysis step (Va), water is added to the aloe mesophyll enzymatically-degraded liquid obtained in the enzymatic degradation step (III) to conduct membrane filtration. By carrying out the dialysis step (Va) involving adding water and conducting the membrane filtration, the organic acid salts and the mineral salts contained in the aloe mesophyll solution can efficiently be recovered into the permeate side of the membrane filtration. While the amount of the water added here is not limited particularly, it is preferable to add water in an amount 1.5 times the original liquid for carrying out the dialysis step (Va) in view of the efficiency of organic acid removal and salt removal, bacterial contamination risk during membrane processing step, operation efficiency of the membrane processing time, and the like.

The concentration step (Vb) is a step for subjecting the aloe mesophyll enzymatically-degraded liquid which completed the dialysis step (Va) to membrane filtration and recovering the satisfactorily water-dispersible aloe extract into the retentate fraction. Thus, the dispersed particles containing β-sitosterol, phospholipids, and dietary fibers is concentrated into the side of the retentate fraction. The concentration magnification in the concentration step (Vb) is not limited particularly, and can be adjusted as appropriate depending on the purpose. In the present technology, a concentration magnification of 2 times or more is preferable in view of the drying efficiency in the drying step (VI) described below.

As discussed above, it is possible, in the manufacturing method according to the present technology, to allow the organic acid salts and the mineral salts contained in the aloe mesophyll solution to be efficiently recovered into the permeate side of the membrane filtration while allowing the dispersed particles containing β-sitosterol, phospholipids, and dietary fibers to be efficiently concentrated into the side of the retentate fraction by carrying out the 2 steps, namely, the dialysis step (Va) and the concentration step (Vb) in the membrane filtration step (V).

The manufacturing method according to the present technology is characterized in that, during its manufacturing steps, no organic solvent extraction or supercritical extraction is conducted. Accordingly, the aloe extract thus produced allows β-sitosterol, which is ordinarily difficult to be miscible with water, to exist in a state similar to that in natural environment. Thus, β-sitosterol and phospholipids which are predominant in a cell membrane exist while allowing the state in which they form a lipid bilayer membrane to be maintained. Accordingly, the aloe extract produced by the manufacturing method according to the present technology exhibits an extremely satisfactory water dispersibility in water. In a preferred embodiment, the aloe extract produced by the manufacturing method according to the present technology has a particle size distribution of the particles in this relevant aloe extract which is characterized by a median size of 100 μm or less and a 90% particle size of 200 μm or less.

In the manufacturing method according to the present technology, its manufacturing steps do not involve filtration using an adsorbent such as an activated charcoal or immersion in an aqueous solution, thereby avoiding any elimination of the aloe-derived dietary fiber during the manufacturing steps. As a result, a satisfactorily water-dispersible aloe extract which contains a sufficient amount of the aloe-derived dietary fibers as functional components can be obtained.

(7) Drying Step (VI)

The drying step (VI) is a step for drying the satisfactorily water-dispersible aloe extract obtained in the membrane filtration step (V) thereby recovering the dried matter of the satisfactorily water-dispersible aloe extract, and carried out for obtaining the dried matter of the satisfactorily water-dispersible aloe extract obtained in the retentate fraction in the membrane filtration step (V).

The typical drying method conducted in the drying step (VI) is not limited particularly as long as a dried matter of the satisfactorily water-dispersible aloe extract can be obtained, and any one or more of known drying methods can be selected and employed. For example, freeze drying and spray drying are contemplated. It is also possible, for reducing the drying time period, to subject the satisfactorily water-dispersible aloe extract obtained in the membrane filtration step (V) further to vacuum evaporation concentration or freezing concentration thereby reducing the water content before conducting the drying step (VI).

(8) Grinding Step (VII)

The grinding step (VII) is a step, after the drying step (VI), for grinding the aforementioned satisfactorily water-dispersible aloe-extracted dried matter. In the manufacturing method according to the present technology, this grinding step (VII) may not particularly be carried out when the dried matter of the satisfactorily water-dispersible aloe extract obtained in the drying step (VI) is applied to the use for which it can be used as it is, but is preferably carried out when the processability into a food is desired to be improved by grinding into finer particles.

The typical grinding method conducted in the grinding step (VII) is not limited particularly as long as a powder of the satisfactorily water-dispersible aloe-extracted dried matter can be obtained, and any one or more known grinding methods can be selected and employed. For example, a method using a grinder such as a jet mill grinder, pin grinder, impact grinder, and the like may be exemplified.

<Aloe Extract>

A liquid aloe extract according to the present technology is an aloe extract which allows an aloe mesophyll-derived solid content to exist as dispersed particles containing β-sitosterol, phospholipids, and dietary fibers in a solution without undergoing precipitation or aggregation. The aloe extract according to the present technology allows β-sitosterol, which is ordinarily difficult to be miscible with water, to exist in a state similar to that in natural environment. Thus, β-sitosterol and phospholipids which are predominant in a cell membrane exist while allowing the state in which they form a lipid bilayer membrane to be maintained. Accordingly, the aloe extract according to the present technology has extremely satisfactory water dispersibility. As a result, the aloe extract according to the present technology is extremely excellent in terms of processability into a food.

In addition, the satisfactorily water-dispersible aloe extract according to the present technology does not allow, during its manufacturing steps, the aloe-derived dietary fiber to be removed. Accordingly, the satisfactorily water-dispersible aloe extract according to the present technology contains an extremely large amount of aloe-derived dietary fibers as functional components when compared with conventional aloe extracts. As a result, it can be applied preferably to a functional food product.

In addition, the satisfactorily water-dispersible aloe extract according to the present technology exhibits a satisfactory flavor because of reduced amounts of organic acid salts and mineral salts contained, and also exhibits a satisfactory flowability of the powder. Accordingly, it allows, when added to a food such as a tablet candy, the flavor of the food to be easily adjusted. Its high flowablity of the powder is also advantageous, for example, when it is used in a food such as a tablet candy, because of easy tablet compaction and readily operable tablet compaction which enables easy tableting.

While the concentration of β-sitosterol contained in the satisfactorily water-dispersible aloe extract according to the present technology is not limited particularly as long as a dispersed particles of β-sitosterol and phospholipids is formed, it is preferable, in view of purification efficiency, that the β-sitosterol content based on the solid content of the aloe extract is 2.5 mg/g or more and 7.5 mg/g or less, more preferably 3.5 mg/g or more and 6.5 mg/g or less.

While the concentration of the dietary fibers contained in the satisfactorily water-dispersible aloe extract according to the present technology is not limited particularly as long as a dispersed particles containing β-sitosterol, phospholipids, and dietary fibers is formed, it is preferable, in view of purification efficiency, that the dietary fiber content based on the solid content of the aloe extract is 400 mg/g or more and 900 mg/g or less, more preferably 450 mg/g or more and 850 mg/g or less, further preferably 500 mg/g or more and 800 mg/g or less.

While the concentration of phospholipids contained in the satisfactorily water-dispersible aloe extract according to the present technology is not limited particularly as long as a dispersed particles of β-sitosterol and phospholipids is formed, it is preferable that the phospholipid content based on the solid content of the aloe extract is 2.5 mg/g or more and 7.5 mg/g or less, more preferably 3.5 mg/g or more and 6.5 mg/g or less.

While the concentration of the organic acid salts contained in the satisfactorily water-dispersible aloe extract according to the present technology is not limited particularly as long as the effect of the present technology is not affected adversely, it is preferable, for reducing an acidic taste, that the concentration of malic acid as an organic acid salt based on the solid content of the aloe extract is 80 mg/g or less.

While the concentration of the mineral salts contained in the satisfactorily water-dispersible aloe extract according to the present technology is not limited particularly as long as the effect of the present technology is not affected adversely, it is preferably 100 mg/g or less based on the solid content of the aloe extract for improving the flavor and reducing the hygroscopicity thereby improving the flowability of the powder.

While the particle size distribution of the particles contained in the satisfactorily water-dispersible aloe extract according to the present technology is not limited particularly as long as the effect of the present technology is not affected adversely, it is preferable that the median size is 100 μm or less and the 90% particle size is 200 μm or less.

While the method for manufacturing aloe extract according to the present technology described above is not limited particularly as long as the effect of the present technology is not affected adversely and any one or more known methods for manufacturing aloe extracts can be employed in combination, the aforementioned manufacturing method according to the present technology can preferably be employed.

EXAMPLES

Hereinafter the present invention is described in further detail based on Examples. The Examples described below merely exemplify representative Examples of the present invention, by which the scope of the present invention is not interpreted narrowly.

Experimental Example 1

<Screening for Polysaccharide-degrading Enzyme>

In Experimental Example 1, screening was conducted for polysaccharide-degrading enzyme formulations which are optimal for degradation of polysaccharides contained in the aloe mesophyll.

(1) Preparation and Homogenization of Aloe Mesophyll Solution

From a raw leaf of Aloe vera, the skin was peeled off, and the mesophyll part was taken out, and cut by a cutter to obtain a mesophyll of Aloe vera, which was subjected to hot air drying to obtain a dried Aloe vera gel. The resultant dried Aloe vera gel was cut into finer particles using a mill to obtain a dried Aloe vera gel powder (Aloe Vera Gel Powder; AVGP). 1 kg of the dried Aloe vera gel powder was combined with 20 kg of ion exchange water and stirred using a homomixer (trade name: Homomixer MARK Model II 2.5, manufactured by PRIMIX Corporation) at 12000 rpm for 30 minutes to achieve homogeneity. This was employed as an aloe mesophyll solution (aloe mesophyll concentration: about 4.8%).

(2) Enzymatic Degradation

As polysaccharide-degrading enzymes, 5 food-oriented polysaccharide-degrading enzyme formulations (cellulase A, cellulase T, hemicellulase 90, pectinase G, pectinase PL: all manufactured by Amano Enzyme Inc., same applied hereinafter) were provided. Six 300-mL conical flasks each containing 210 g of the aloe mesophyll solution were provided (5 enzyme-supplemented samples and an enzyme-free sample). 40 g of an aqueous solution of the enzyme containing each enzyme formulation corresponding to 1 g of the enzyme was prepared, and placed in the conical flask containing the aloe mesophyll solution immediately before starting enzymatic degradation (final aloe mesophyll concentration: 4%). To the enzyme-free sample, 40 g of ion exchange water was added. The enzymatic degradation was conducted in an incubator at 50° C. and 140 rpm for 20 hours. After certain time period, the enzyme was inactivated by heating in a water bath at 100° C. for 10 minutes. Immediately after heating, the sample was cooled with ice.

(3) Viscosity Measurement

The aloe mesophyll solution after cooling with ice after completing the enzymatic degradation was allowed to warm again to room temperature (20° C.), and its viscosity was measured using a vibration-type viscometer (VIBRO VISCOMETER CJV5000; manufactured by A&D Company, Limited). As a control, a sample made from the aloe mesophyll solution as an aqueous solution having an aloe mesophyll concentration of 4% using ion exchange water was employed.

(4) Results

The results of the viscosity measurement are indicated in Table 1 shown below. While every enzyme formulation reduced the viscosity of the aloe mesophyll solution, one which gave the maximum reduction in the viscosity of the aloe mesophyll solution was hemicellulase 90. Based on the results of Experimental Example 1, it was discovered that the polysaccharide-degrading enzyme employed in the manufacturing method according to the present technology may be any of various polysaccharide-degrading enzymes, among which hemicellulase is preferable.

TABLE 1

|  | pH | Viscosity (mPa · s) | Temperature at measurement (° C.) |
| --- | --- | --- | --- |
| Control | 4.57 | 86.7 | 20.0 |
| Cellulase A | 4.23 | 1.7 | 24.6 |
| Cellulase T | 6.49 | 3.1 | 24.4 |
| Hemicellulase 90 | 4.21 | 1.5 | 24.5 |
| Pectinase G | 4.25 | 1.6 | 24.5 |
| Pectinase PL | 4.33 | 1.9 | 24.4 |

Experimental Example 2

<Study 1 of Amount of Polysaccharide-degrading Enzyme to be Added>

In Experimental Example 2, the amount of the polysaccharide-degrading enzyme to be added which is optimal for the degradation of the polysaccharides contained in the aloe mesophyll was studied. In this Experimental Example, hemicellulase was employed as an example of the polysaccharide-degrading enzymes.

(1) Preparation and Homogenization of Aloe Mesophyll Solution

By the method similar to that in Experimental Example 1, an aloe mesophyll solution was prepared.

(2) Enzymatic Degradation

Each 210 g of the aloe mesophyll solution was placed in a 300-mL conical flask, and 40 g of the enzyme solution containing hemicellulase 90 was added immediately before starting enzymatic degradation (250 g in total, final aloe mesophyll concentration: 4%). The hemicellulase concentration of the enzyme solution was adjusted so that the enzyme amount based on the aloe mesophyll became 1% (0.1 g), 0.1% (0.01 g), 0.01% (0.001 g), and 0.001% (0.0001 g). When these amounts are converted into the formulation amounts, the formulation amounts contained in 40 g of the enzyme solution were 0.17 g, 0.017 g, 0.0017 g, and 0.00017 g, respectively, because hemicellulase 90 contains 60% enzyme. In the enzyme-free sample, only ion exchange water was added. The enzymatic degradation was conducted in an incubator under a condition at 50° C. and 140 rpm for 1 hour. After completion of the enzymatic degradation, the enzyme was inactivated by heating in a water bath at 100° C. for 10 minutes. Immediately after inactivation, the sample was cooled with ice.

(3) Viscosity Measurement

By the method similar to that in Experimental Example 1, the viscosity of each aloe mesophyll solution was measured.

(4) Results

The results are shown in FIG. 2. As shown in FIG. 2, it was found that the aloe mesophyll solution can be adjusted at any desirable viscosity depending on the amount of the enzyme added. While the viscosity of the sample containing 0.001% polysaccharide-degrading enzyme based on the aloe mesophyll was about 40mPa·s, this viscosity enables continuous membrane filtration. Between the viscosities of the sample containing 1% polysaccharide-degrading enzyme and the sample containing 10% polysaccharide-degrading enzyme based on the aloe mesophyll, there was not such a difference that may affect the membrane filtration step. Based on the results of Experimental Example 2, it was found that it is preferable to use 1.0% by mass or less of the polysaccharide-degrading enzyme based on the aloe mesophyll solid amount.

Experimental Example 3

<Study 2 of Amount of Polysaccharide-degrading Enzyme to be Added>

In Experimental Example 3, the effect of the amount of the polysaccharide-degrading enzyme added on the amounts of the polysaccharides, aloe mesophyll-derived phytosterol (β-sitosterol), and malic acid contained in the aloe extract was investigated. In this Experimental Example, hemicellulase was employed as an example of the polysaccharide-degrading enzymes.

(1) Preparation and Homogenization of Aloe Mesophyll Solution

By the method similar to that in Experimental Example 1, an aloe mesophyll solution was prepared.

(2) Enzymatic Degradation

By the method similar to that in Experimental Example 2, the polysaccharides contained in the aloe mesophyll solution were subjected to enzymatic degradation.

(3) Membrane Filtration 300 g of each aloe mesophyll solution which had completed the enzymatic degradation was then subjected to an ultrafiltration device (FILTRATON SYSTEM PS-24001; manufactured by Asahi Kasei Chemicals Corporation). As an ultrafiltration membrane, a polysulfone hollow fiber membrane SIP-0013 (nominal molecular weight cut-off 6000; manufactured Asahi Kasei Chemicals Corporation) was employed. Pump output was adjusted at 30%, and the back pressure memory was adjusted at 2. The ultrafiltration was continued while adding 50 ml of the ion exchange water to the retentate upon each 50 ml discharge of the permeate until the permeate in an amount 1.5 times the original liquid (450 mL) was discharged.

(4) Measurement of Weight, Solid Concentration, Viscosity, and pH

The retentates and permeates obtained by the membrane filtration were examined for their weight, solid concentration, viscosity, and pH. The viscosity was measured by the method similar to that employed in Experimental Example 1.

(5) Drying

The retentate fractions (aloe extract) which had been subjected to the aforementioned various measurements were freeze dried according to an ordinary method.

(6) Analysis of Molecular Weight Distribution of Polysaccharides

The aloe-extracted dried matter obtained by the freeze drying was extracted with water, and then subjected to the gel filtration chromatography to analyze the molecular weight distribution of polysaccharides. The molecular weight was determined based on the calibration curve of a dextran standard. While the amount of the polysaccharide contained in the original raw material (dried Aloe vera gel powder) was regarded as 1, the relative value of the water-soluble polysaccharides contained in each sample was calculated. The results are shown in FIG. 3.

It was found that when adding 1% or more of the enzyme is added based on the aloe mesophyll, the polysaccharides of 10,000 Da or more were eliminated. On the other hand, it was also found that when the amount of the enzyme was restricted to 0.1% or less based on the aloe mesophyll and the concentration was conducted by the ultrafiltration, new polysaccharides having molecular weights of 11600 Da to 410000 Da was detected.

(7) Quantification of β-Sitosterol

After extracting liposoluble components from the aloe-extracted dried matter obtained by the freeze drying, the β-sitosterol content was quantified by a gas chromatograph-mass spectrometer. The quantification was conducted based on the calibration curve made using standards. Similarly, the β-sitosterol content of the original raw material (dried Aloe vera gel powder) was also quantified. The results are indicated in Table 2 shown below.

TABLE 2

|  |  | β-Sitosterol content (mg/g) |
| --- | --- | --- |
| Raw material (Aloe vera gel powder) |  | 1.5 |
| Amount of enzyme added (%) | 1 | 4.5 |
|  | 0.1 | 3.8 |
|  | 0.01 | 3.2 |

As shown in Table 2, it was found that by adding 0.01% or more of the enzyme based on the aloe mesophyll, the β-sitosterol can be concentrated up to a level 2 times that of the original raw material or more.

(8) Quantification of Cyclolanostane Compounds and Lophenol Compounds

The aloe-extracted dried matter obtained by the freeze drying was subjected to a liquid chromatograph-mass spectrometer to quantify cyclolanostane compounds (2 compounds; 9,19-cyclolanostane-3-ol, 24-methylene-9,19-cyclolanostane-3-ol) and lophenol compounds (3 compounds; 4-methylcholest-7-en-3-ol, 4-methylergost-7-en-3-ol, 4-methylstigmast-7-en-3-ol). The quantification was conducted based on the calibration curve made using standards. The results are indicated in Table 3 shown below.

TABLE 3

| | Cyclolanostane compounds (µg/g) | | Lophenol compounds (µg/g) | | |
|---|---|---|---|---|---|
| | 9,19-Cyclo-lanostane-3-ol | 24-Methylene-9,19-cyclo-lanostane-3-ol | 4-Methyl-cholest-7-en-3-ol | 4-Methyl-ergost-7-en-3-ol | 4-Methyl-stigmast-7-en-3-ol |
| Raw material (Aloe vera gel powder) | 31.8 | 20.3 | 19.0 | 22.1 | 16.9 |
| | | 52.1 | | 58.0 | |
| | Ratio based on raw material: 1 | | Ratio based on raw material: 1 | | |
| 0.1% Enzyme-containing sample | 61.8 | 44.8 | 33.5 | 41.1 | 32.8 |
| | | 106.6 | | 107.4 | |
| | Ratio based on raw material: 2.0 | | Ratio based on raw material: 1.9 | | |
| 0.01% Enzyme-containing sample | 55.1 | 37.9 | 28.2 | 33.5 | 25.6 |
| | | 93.1 | | 87.3 | |
| | Ratio based on raw material: 1.8 | | Ratio based on raw material: 1.5 | | |

As shown in Table 3, it was found that by adding 0.01% or more of the enzyme based on the aloe mesophyll, the cyclolanostane compounds and the lophenol compounds can be concentrated up to a level 1.5 times that of the original raw material or more.

(9) Quantification of Malic Acid

The aloe-extracted dried matter obtained by the freeze drying was subjected to a gas chromatograph-mass spectrometer to quantify malic acid. The quantification was conducted based on the calibration curve made using standards. The results are indicated in Table 4 shown below.

TABLE 4

| | | Malic acid content (mg/g) |
|---|---|---|
| Raw material (Aloe vera gel powder) | | 125.8 |
| Amount of enzyme added (%) | 1 | 56.5 |
| | 0.1 | 43.9 |
| | 0.01 | 39.6 |

As shown in Table 4, it was found that by adding 0.01 to 1% of the enzyme based on the aloe mesophyll followed by the ultrafiltration, the amount of malic acid in the retentate fraction can be reduced to a level half that in the original raw material or less.

Experimental Example 4

<Investigation of Aloe Extract Manufacturing Steps>

In Experimental Example 4, the combination of various steps in the manufacturing steps for producing the aloe extract, namely enzymatic degradation, ultrafiltration, filter paper filtration, activated charcoal treatment, and hydrochloric acid degradation, was investigated for its effect on the composition and the characteristics of the aloe extract.

(1) Preparation and Homogenization of Aloe Mesophyll Solution

By the method similar to that in Experimental Example 1, the aloe mesophyll solution of Samples 1 to 21 were prepared.

(2) Enzymatic Degradation

To each aloe mesophyll solution of Samples 2 to 10, 12 and 14 to 18, the polysaccharide-degrading enzyme (hemicellulase 90) was added in the amounts indicated in Table 5 shown below, and the enzymatic degradation of the polysaccharide contained in the aloe mesophyll solution was conducted by the method similar to that in Experimental Example 2.

(3) Hydrochloric Acid Degradation

Each aloe mesophyll solution of Samples 19 to 21 was supplemented with 0.7% of hydrochloric acid based on the aloe mesophyll, and hydrochloric acid degradation was conducted under a condition at 85° C. for 0.5 hours. Thereafter, the pH was measured and neutralization was carried out using a 20% sodium hydroxide solution. The hydrochloric acid level of 0.7% based on the aloe mesophyll is an amount which gives a viscosity equivalent to that achieved by adding the polysaccharide-degrading enzyme (hemicellulase 90) at 0.1% based on the aloe mesophyll.

(4) Activated Charcoal Treatment

To 1 kg of each aloe mesophyll solution of samples 13, 14, 16, and 18 (after completing enzymatic degradation except for Sample 13), 20 g of activated charcoal was added and the activated charcoal treatment was conducted with stirring at room temperature for 1 hour. Then a filter paper (ADVANTEC, No.1) was used for filtration with suction, and the filtrate was further filtered with suction using a filter paper (ADVANTEC, No.7) thereby removing the activated charcoal. The filtrate obtained was employed as an activated charcoal-treated solution.

(5) Filter Paper Filtration

Each aloe mesophyll solution of Samples 11 to 18 was filtered through a filter paper according to an ordinary method (after completing enzymatic degradation in Samples 12, 15, and 17 and after completing activated charcoal treatment in Samples 13, 14, 16, and 18).

(6) Ultrafiltration

Each aloe mesophyll solution of Samples 5 to 10, 15 to 18, 20 and 21 was subjected to ultrafiltration (after completing enzymatic degradation in Samples 5 to 10, after filter paper filtration in Samples 15 to 18, and after hydrochloric acid degradation in Samples 20 and 21) by the method similar to that in Experimental Example 3. The retentate fractions of Samples 5 to 7, 15, 16, and 20 and the permeates of Samples 8 to 10, 17, 18, and 21 were used in the subsequent analysis.

(7) Drying

Each of Samples 2 to 21 which had completed the aforementioned various steps was freeze dried according to an ordinary method. For Sample 1, the dried Aloe vera gel powder which was the raw material was used as a control as it was.

(8) β-Sitosterol Quantification

Each sample was examined for its β-sitosterol content by the method similar to that in Experimental Example 3.

(9) Measurement of Angle of Repose and FlowAbility Evaluation

Each sample after being freeze dried was milled for 1 minute to obtain a fine powder. The angle of repose of the fine powder of each sample was measured according to an ordinary method. When an agglomerate of the powder due to moisture absorption or aggregation was observed, then the sample was indicated as "measurement impossible". The flowability evaluation was conducted referring to Carr's classification (Carr,R.L.:Evaluating flow properties of solids., Chem. Eng., 1965; 72:163-168).

(10) Malic Acid Quantification

The malic acid content of each sample was quantified by the method similar to that in Experimental Example 3.

(11) Flavor Intensity Evaluation 0.5 g of each freeze dried sample was given to 10 panelists who were blinded to the sample name, and the flavor intensity was evaluated based on the 5-rank evaluation shown below. The mean value of the evaluation scores given by 10 panelists was regarded as the evaluation value.

Score 4: Extremely intense flavor is sensed.
Score 3: Intense flavor is sensed.
Score 2: Flavor is sensed.
Score 1: Flavor is poorly sensed.
Score 0: Flavor is not sensed at all.

(12) Results

The respective step procedures for each sample, the compositions and characteristics measured and evaluated as described above are indicated in Table 5 shown below. In Table 5, "nd" is marked for the sample below detection limit.

TABLE 5

| | | Sample No. | | | | | | |
|---|---|---|---|---|---|---|---|---|
| | | 1 | 2 | 3 | 4 | 5 | 6 | 7 |
| Steps | Enzymatic degradation | — | 1% | 0.10% | 0.01% | 1% | 0.10% | 0.01% |
| | Hydrochloric acid degradation | — | — | — | — | — | — | — |
| | Activated charcoal treatment | — | — | — | — | — | — | — |
| | Filter paper filtration | — | — | — | — | — | — | — |
| | Ultrafiltration | — | — | — | — | Retentate fraction | Retentate fraction | Retentate fraction |
| Angle of repose (°) | | 60 | 43 | 46 | 53 | 38 | 40 | 49 |
| β-Sitosterol (mg/g) | | 2.17 | 2.25 | 2.41 | 2.31 | 6.02 | 5.38 | 3.61 |
| Ratio based on raw material | | 1 | 1.04 | 1.11 | 1.06 | 2.77 | 2.48 | 1.66 |
| Malic acid (mg/g) | | 128.2 | 121 | 117.1 | 112.4 | 62 | 54.6 | 43.5 |
| Ratio based on raw material | | 1 | 0.94 | 0.91 | 0.88 | 0.48 | 0.43 | 0.34 |
| Flavor intensity | | 3.6 | 3.4 | 2.6 | 2.4 | 1.9 | 0.6 | 0.8 |

| | | Sample No. | | | | | | |
|---|---|---|---|---|---|---|---|---|
| | | 8 | 9 | 10 | 11 | 12 | 13 | 14 |
| Steps | Enzymatic degradation | 1% | 0.10% | 0.01% | — | 0.10% | — | 0.10% |
| | Hydrochloric acid degradation | — | — | — | — | — | — | — |
| | Activated charcoal treatment | — | — | — | — | — | Activated charcoal | Activated charcoal |
| | Filter paper filtration | — | — | — | Filter paper filtrate | Filter paper filtrate | Filter paper filtrate | Filter paper filtrate |
| | Ultrafiltration | Permeate | Permeate | Permeate | — | — | — | — |
| Angle of repose (°) | | Measurement impossible | Measurement impossible | Measurement impossible | Measurement impossible | 51 | Measurement impossible | 50 |
| β-Sitosterol (mg/g) | | — | — | — | — | 1.12 | — | 0.17 |
| Ratio based on raw material | | — | — | — | — | 0.52 | — | 0.08 |
| Malic acid (mg/g) | | — | — | — | — | 150 | — | 180 |
| Ratio based on raw material | | — | — | — | — | 1.17 | — | 1.40 |
| Flavor intensity | | — | — | — | — | 3.2 | — | 2.6 |

| | | Sample No. | | | | | | |
|---|---|---|---|---|---|---|---|---|
| | | 15 | 16 | 17 | 18 | 19 | 20 | 21 |
| Steps | Enzymatic degradation | 0.10% | 0.10% | 0.10% | 0.10% | — | — | — |
| | Hydrochloric acid degradation | — | — | — | — | 0.70% | 0.70% | 0.70% |

TABLE 5-continued

| | | | | | | | |
|---|---|---|---|---|---|---|---|
| Activated charcoal treatment | — | Activated charcoal | — | Activated charcoal | — | — | — |
| Filter paper filtration | Filter paper filtrate | Filter paper filtrate | Filter paper filtrate | Filter paper filtrate | — | — | — |
| Ultrafiltration | Retentate fraction | Retentate fraction | Permeate | Permeate | — | Retentate fraction | Permeate |
| Angle of repose (°) | 55 | Measurement impossible | 53 | 46 | 46 | 43 | Measurement impossible |
| β-Sitosterol (mg/g) | 2.07 | — | nd | nd | 1.92 | 3.44 | — |
| Ratio based on raw material | 0.95 | — | — | — | 0.88 | 1.59 | — |
| Malic acid (mg/g) | 115.5 | — | — | — | 123.8 | 84.2 | — |
| Ratio based on raw material | 0.90 | — | — | — | 0.97 | 0.66 | — |
| Flavor intensity | 2.1 | — | — | — | 3.2 | 3.0 | — | a. β-Sitosterol

As shown in Table 5, the dried Aloe vera gel powder (Sample 1) as a raw material contained 2.17 mg/g of β-sitosterol. On the other hand, the amount of β-sitosterol in Samples 2 to 4 and Sample 19 which had been subjected only to the enzymatic degradation or hydrochloric acid degradation was not substantially changed, indicating that the enzymatic degradation or hydrochloric acid degradation causes almost no change in the amount of β-sitosterol.

In Samples 5 to 7 and 20 which recovered the retentate fractions as aloe extracts by a combination of the enzymatic degradation or hydrochloric acid degradation and the ultrafiltration, β-sitosterol was concentrated by 1.5 to 2.7 times when compared with the dried Aloe vera gel powder (Sample 1) as a raw material. On the other hand, Samples 11 to 18 which combined the activated charcoal treatment and the filter paper filtration exhibited reduced amounts of β-sitosterol when compared with the dried Aloe vera gel powder (Sample 1) as a raw material. Even when combining the enzymatic degradation or hydrochloric acid degradation and the ultrafiltration, Samples 8 to 10 and 21 which recovered the permeates as aloe extracts were not successful in measuring β-sitosterol. Based on these results, it was proven that, in order to concentrate the aloe-derived β-sitosterol, it is preferable to obtain the retentate fraction by conducting the enzymatic degradation and the ultrafiltration without conducting filtration steps such as the activated charcoal treatment or the filter paper filtration.

b. Angle of Repose and Flowability

The dried Aloe vera gel powder (Sample 1) as a raw material had an angle of repose of 60° which indicated an extremely poor flowability. Comparison among Samples 2 to 4 which conducted the enzymatic degradation indicated a relatively good flowability exhibited by Sample 2 to which 1% of the enzyme was added based on the raw material. Samples 5 to 7 which recovered the retentate fractions as aloe extracts by the ultrafiltration after the enzymatic degradation all exhibited low angles of repose reflecting their improved flowability when compared with Samples 2 to 4 which did not conduct the ultrafiltration. Among these, Sample 5 which recovered the retentate fraction as an aloe extract by the ultrafiltration after degradation with the enzyme at 1% exhibited the highest flowability.

Samples 8 to 10 which recovered permeates as aloe extracts by the ultrafiltration were not successful in measuring the angle of repose because of their tendency to form agglomerates due to moisture absorption. Thus, the flowability was poor. Samples 11 and 13 obtained by completing the filter paper filtration and/or the activated charcoal treatment were not successful in measuring the angle of repose because of their tendency to form agglomerates due to moisture absorption. Thus, the flowability was poor. Sample 20 which recovered the retentate fraction as an aloe extract by the ultrafiltration after the hydrochloric acid degradation exhibited a flowability similar to that of Sample 2 which completed only the enzymatic degradation at 1%.

c. Malic Acid

The dried Aloe vera gel powder (Sample 1) as a raw material contained 128.2 mg/g of malic acid. Samples 5 to 7 which recovered the retentate fractions as aloe extracts by the ultrafiltration after the enzymatic degradation all had malic acid contents which were reduced to a half or less of that in the raw material. On the other hand, Samples 12 and 14 obtained by completing the filter paper filtration and/or the activated charcoal treatment after the enzymatic degradation had malic acid contents which had been concentrated when compared with the raw material. Based on these results, it was proven that, in order to reduce the malic acid content of the aloe extract, it is necessary to obtain the retentate fraction after conducting the enzymatic degradation and the ultrafiltration.

d. Flavor

The dried Aloe vera gel powder (Sample 1) as a raw material had an unique herbal odor, bitter taste, acidic taste, and the like, and exhibited a flavor intensity of Score 3.6 which was the highest. Samples 2 to 4 which conducted only the enzymatic degradation also exhibited remaining unique herbal odor, bitter taste, acidic taste, and the like, thus being unsuccessful in substantially suppressing the flavor. Sample 12 obtained only by the filter paper filtration after the enzymatic degradation also exhibited remaining unique herbal odor, bitter taste, acidic taste, and the like, thus being unsuccessful in substantially suppressing the flavor. Sample 14 which completed the filter paper filtration and the activated charcoal treatment after the enzymatic degradation had a suppressed unique herbal odor, but still exhibited an intense saltiness, acidic taste, and the like. Sample 19 which completed only the hydrochloric acid degradation had a remaining unique herbal odor, an intense saltiness, and a slight stimulation due to hydrochloric acid. Sample 20 which recovered the retentate fraction as an aloe extract by the ultrafiltration after the hydrochloric acid degradation had a suppressed unique herbal odor, but still exhibited an intense saltiness and a slight stimulation due to hydrochloric acid. On the other hand, Samples 5 to 7 which recovered the retentate fractions as aloe extracts by the ultrafiltration after the enzymatic degradation all exhibited reduced flavor intensities.

Based on these results, it was proven that, in order to obtain an aloe extract whose flavors such as herbal odor, bitter taste, and acidic taste were suppressed, it is necessary to obtain the retentate fraction by conducting the enzymatic degradation and the ultrafiltration. It was also found that since the aloe extract according to the present technology had reduced unique flavors, it allows, when added to a food, a flavor inherent in such a food to be adjusted easily.

Experimental Example 5

<Investigation of Dispersibility into Water>

The dispersibilities of the aloe extract according to the present technology and the aloe supercritical carbon dioxide extract into water were compared.

(1) Preparation of Aloe Supercritical Carbon Dioxide Extract

Leaf skin of 60 kg of Aloe vera was peeled off to recover a mesophyll part, and the recovered mesophyll part was freeze dried to prepare 300 g of Aloe vera mesophyll powder. Then, 20 g of the Aloe vera mesophyll powder thus prepared was employed to conduct extraction by a supercritical extraction method. The supercritical extraction was conducted using CO2 delivery pump (SCF-GET), PU-2080 pump (PU-2080 plus), Back Pressure Regulator (SCF-BPG) manufactured by JASCO Corporation and a flange manufactured by Toyo Koatsu Inc. together with carbon dioxide gas as an extraction solvent.

(2) Comparison of Dispersibility

Sample 6 prepared in Experimental Example 4 and the supercritical carbon dioxide extract prepared as described above were added to water to form 0.5% (w/w) aqueous solutions, and the dispersibilities of the both into water were compared. The results are shown in FIG. 4. A in FIG. 4 is a drawing-substituting photograph showing the state after agitation using a stirrer for 3 minutes while B is a drawing-substituting photograph showing the state after agitation using a stirrer for 3 minutes followed by ultrasonic treatment for 5 minutes. As shown in FIG. 4, the aloe extract according to the present technology (Sample 6) was dispersed readily in water, while the supercritical carbon dioxide extract allows insolubles to remain even after ultrasonication.

Then, the aloe extract according to the present technology (Sample 6) and the supercritical carbon dioxide extract were added to water so that the β-sitosterol content of the aqueous solutions became the same and their dispersibilities into water were compared. Since Sample 6 prepared in Experimental Example 4 contained 5.38 mg/g of β-sitosterol while the supercritical carbon dioxide extract contained 255.6 mg/g, 0.5 g of Sample 6 was added to 100 mL of water while 0.01 g of the supercritical carbon dioxide extract was added. When the dispersibilities of these were compared, the aloe extract according to the present technology (Sample 6) was dispersed readily in water while the supercritical carbon dioxide extract allows insolubles to remain even after ultrasonication. Based on these results, it was found that the aloe extract according to the present technology has a water dispersibility which is far higher than that of an extract obtained by purifying β-sitosterol from an aloe by a conventional method.

Experimental Example 6

<Study of Membrane Used in Membrane Filtration Step>

In Experimental Example 6, a microfiltration membrane was used instead of the ultrafiltration membrane as a membrane employed in the membrane filtration step, and the effects on the composition and the characteristics of the aloe extract were investigated.

(1) Preparation/Homogenization of Aloe Mesophyll Solution

By the method similar to that in Experimental Example 1, the aloe mesophyll solutions of Samples 22 and 23 were prepared.

(2) Enzymatic Degradation

To the aloe mesophyll solutions of Samples 22 and 23, 0.1% of the polysaccharide-degrading enzyme (hemicellulase 90) was added based on the aloe mesophyll, and the enzymatic degradation of the polysaccharides in the aloe mesophyll solution was conducted by the method similar to that in Experimental Example 2.

(3) Microfiltration

The aloe mesophyll solutions of Samples 22 and 23 which completed the enzymatic degradation were subjected to microfiltration (pore size: 0.25 μm) treatment according to an ordinary method.

(4) Measurement of Various Components and Evaluation of Characteristics

By the methods similar to those in Experimental Example 4, quantification of β-sitosterol and malic acid, measurement of angle of repose, flowability evaluation, and flavor intensity evaluation were conducted.

(5) Results

The results are indicated in Table 6 shown below.

TABLE 6

| | Sample No. | 22 | 23 |
|---|---|---|---|
| Steps | Enzymatic degradation | 0.10% | 0.10% |
| | Hydrochloric acid degradation | — | — |
| | Activated charcoal treatment | — | — |
| | Filter paper filtration | — | — |
| | Microfiltration | Retentate fraction | Permeate |
| Angle of repose (°) | | 42 | Measurement impossible |
| β-Sitosterol (mg/g) | | 7.33 | — |
| Ratio based on raw material | | 3.38 | — |
| Malic acid (mg/g) | | 55.3 | — |
| Ratio based on raw material | | 0.43 | — |
| Flavor intensity | | 1.6 | — |

As shown in Table 6, Sample 22 which recovered the retentate fraction as an aloe extract by the microfiltration after the enzymatic degradation had a reduced angle of repose, β-sitosterol concentrated by 3 times or more, malic acid reduced to a half or less, and a reduced flavor intensity when compared with the dried Aloe vera gel powder (Sample 1 in Experimental Example 4) as a raw material. These results are equivalent or superior to the results observed with Samples 5 to 7 in Experimental Example 4 which recovered the retentate fractions as aloe extracts by the ultrafiltration after the enzymatic degradation. Based on these results, it was found that any of the ultrafiltration membrane and the microfiltration membrane can be employed in the membrane filtration in the manufacturing method according to the present technology.

It is also found that, with regard to the results of the β-sitosterol concentration, Sample 22 which completed the microfiltration achieved a higher concentration magnification when compared with Sample 6 which completed the ultrafiltration. Accordingly, it was found that when aiming at efficiently concentrating the dispersed particles containing β-sitosterol, phospholipids, and dietary fibers it is preferable to use a microfiltration membrane.

Furthermore, it was found that Sample 6 which completed the ultrafiltration was somewhat more satisfactory with regard to the results of measurement of the angle of repose and the flavor intensity when compared with Sample 22 which completed the microfiltration. Accordingly, it was found that when aiming at improving the flavor and improving the flowability of the powder obtained by grinding the produced satisfactorily water-dispersible aloe-extracted dried matter, it is preferable to use an ultrafiltration membrane.

Experimental Example 7

<Study of Angle of Repose and Tablet Compaction Performance>

In Experimental Example 7, it was studied how the difference in the angle of repose is reflected on the tablet compaction performance.

(1) Tablet Making

To each of the dried Aloe vera gel powder (Sample 1 in Experimental Example 4) as a raw material and the freeze dried Samples 5 to 7 in Experimental Example 4, 4 g of citric anhydride, 56.5 g of maltitol, 10 g of crystalline cellulose, 0.5 g of tricalcium phosphate, 2 g of glycerin fatty acid ester, and 2 g of emulsifier were added, and mixed thoroughly and then the raw material was supplied to the hopper of the tablet compaction machine and a tablet was made. The angle of repose was 48° in Sample 1 formulation, 35° in Sample 5 formulation, 37° in Sample 6 formulation, and 41° in Sample 7 formulation. The angles of repose of the dried Aloe vera gel powder (Sample 1 in Experimental Example 4) and the freeze dried Samples 5 to 7 in Experimental Example 4 themselves were 60° in Sample 1, 38° in Sample 5, 40° in Sample 6, 49° in Sample 7, respectively, as indicated in Table 5 shown above.

(2) Evaluation of Tablet Compaction Performance

When the tablet compaction was conducted using Sample 1 formulation, the machine stopped frequently due to tablet compaction pressure errors because of a poor run down from the hopper which prevents an appropriate amount from running down into the tablet compaction zone. In addition, the resultant tablets were problematic because of capping, sticking, and binding. Moreover, the resultant tablets were greatly uneven in their weights. On the other hand, when conducting the tablet compaction using Samples 5 to 7 formulation, the running down from the hopper was satisfactory and the machine did not stop. The resultant tablets were also satisfactory without any nicks or cracks. Based on these results, it was suggested that by using at least an aloe-extracted dried matter having an angle of repose of 49° or less, the tablet compaction can be accomplished without any problem, and it was proven that the aloe-extracted dried matter according to the present technology has a low angle of repose and an excellent flowability and is a powder suitable to the tablet compaction.

Manufacture Example 1

<Manufacture of Aloe Extract According to Present Technology>

In Manufacture Example 1, the aloe extract according to the present technology was manufactured on a practical scale.

(1) Preparation and Homogenization of Aloe Mesophyll Solution

To 4 kg of the dried Aloe vera gel powder obtained by the method similar to that in Experimental Example 1, 80 kg of ion exchange water was added and a supermixer was used for stirring for 15 minutes, thereby homogenizing the aloe mesophyll. This was employed as an aloe mesophyll solution (aloe mesophyll concentration: about 4.8%). The particle size distribution of the particles in this aloe mesophyll solution was measured using a laser diffraction/scattering particle size distribution measuring device (LA-500; manufactured by Horiba Ltd.), and the median size was 92.53 μm and the 90% particle size was 149.93 μm.

(2) Enzymatic Degradation 84 kg of the aloe mesophyll solution prepared as described above was placed in a jacketed tank. Then 16 kg of the enzyme solution containing 6.77 g of hemicellulase 90 (4 g as enzyme, 0.1% by mass based on aloe mesophyll) was further added (100 kg in total). While stirring the solution in the tank using a stirring machine, the enzymatic degradation was conducted at 50° C. for 2 and a half hours. Immediately after completing the enzymatic degradation, steam was introduced into the tank jacket to raise the temperature in the tank to 90° C., at which the temperature was kept for 10 minutes thereby inactivating the enzyme. Immediately after completing the enzyme inactivation, a chilled water was introduced into the tank jacket to lower the temperature in the tank to 4° C.

(3) Membrane Filtration

The enzyme-degraded aloe mesophyll solution was subjected to ultrafiltration. As ultrafiltration steps, a "dialysis step" in which water in an amount 1.5 times the original liquid was added and a "concentration step" in which the original liquid is concentrated by 2 times were conducted. An ultrafiltration membrane whose molecular weight cut-off was 10000 Da (SLP-3053: manufactured by Asahi Kasei Chemicals Corporation) was employed. To a retentate tank, 100 kg of the aloe mesophyll solution which completed the enzymatic degradation and 150 kg of water for dialysis were added. The flow rate of the liquid supplying pump was changed appropriately so that the permeation flow speed became 100 to 120 L/hr. At the time when the permeate amount was 150 kg, the dialysis step was terminated and switched directly to the concentration step. At the time when the permeate amount was 50 kg, the concentration step was terminated (final retentate amount: 50kg, concentration by 2 times). 50 kg of the retentate obtained by the ultrafiltration was kept in a water bath at 90° C. for 30 minutes, thereby accomplishing batch sterilization. This sterilized retentate was recovered as an aloe extract according to the present technology. The particle size distribution of the particles contained in this aloe extract was measured using a laser diffraction/scattering particle size distribution measuring device (LA-500; manufactured by Horiba Ltd.), and the median size was 72.12 pm and the 90% particle size was 136.07 μm.

(4) Drying 50 kg of the aforementioned aloe extract was freeze dried to obtain 2 kg of the aloe-extracted dried matter according to the present technology.

(5) Composition Analysis

The general compositions (proteins, lipids, ashes, and carbohydrates) and the dietary fiber contents of the dried Aloe vera gel powder as a raw material and the obtained aloe-extracted dried matter according to the present technology as described above were compared. The proteins were assayed by Kjeldahl method (nitrogen/protein factor: 6.25). The lipids were measured by acid decomposition method. The ashes were measured by direct ashing method. The carbohydrates were calculated based on the equation in accordance with Nutrition Labelling Standard (Notification No.176 of Ministry of Health, Labor and Welfare in 2003: 100−(water+protein+lipids+ash+dietary fiber). Accordingly, the organic acids such as malic acid are included in the carbohydrate. The dietary fibers were measured by enzymatic-gravimetric method. The results are indicated in Table 7 shown below.

TABLE 7

| Item | Dried Aloe vera gel powder | Aloe-extracted dried matter | Ratio based on raw material |
|---|---|---|---|
| Proteins (%) | 4.1 | 5.8 | 1.4 |
| Lipids (%) | 2.5 | 5.0 | 2.0 |
| Ashes (%) | 14.1 | 7.8 | 0.6 |
| Carbohydrates (%) | 37.3 | 9.9 | 0.3 |
| Dietary fibers (%) | 42.0 | 71.5 | 1.7 |
| Total (%) | 100 | 100 | 1 |

As shown in Table 7, the proteins were concentrated by 1.4 times, the lipids by 2.0 times, and the dietary fibers by 1.7 times in the aloe-extracted dried matter according to the present technology. On the other hand, the ashes were reduced by 40% and the carbohydrates (including organic acids) by 70%. Based on these results, it was proven that it is possible to concentrate the aloe mesophyll-derived phytosterols and to reduce the ashes and the organic acids constituting the aloe's unique flavor without reducing the dietary fiber content of the aloe mesophyll by the manufacturing method according to the present technology.

The present technology can also be in the following constitution.

(1) A method for manufacturing an aloe extract containing β-sitosterol, phospholipids, and dietary fibers which involves carrying out:

a homogenization step for homogenizing an aloe mesophyll solution;

an enzymatic degradation step for adding a polysaccharide-degrading enzyme to the homogenized aloe mesophyll solution and degrading polysaccharides contained in the aforementioned homogenized aloe mesophyll solution; and, a membrane filtration step for membrane-filtering the enzyme-degraded aloe mesophyll solution with a microfiltration membrane or an ultrafiltration membrane and recovering the retentate fraction as an aloe extract.

(2) The method for manufacturing an aloe extract according to (1) wherein the aforementioned enzymatic degradation step is a step for adding 0.01 to 1.0% by mass of the aforementioned polysaccharide-degrading enzyme based on aloe mesophyll non-volatile components contained in the aforementioned homogenized aloe mesophyll solution and degrading polysaccharides contained in the aloe mesophyll solution.

(3) The method for manufacturing an aloe extract according to (1) or (2) wherein the aforementioned polysaccharide-degrading enzyme is a hemicellulase.

(4) The method for manufacturing an aloe extract according to any one of (1) to (3) wherein the aforementioned membrane filtration step is a membrane filtration step for membrane-filtering the aforementioned enzyme-degraded aloe mesophyll solution with a microfiltration membrane and recovering the retentate fraction as an aloe extract.

(5) The method for manufacturing an aloe extract according to any one of (1) to (4) which involves carrying out, before the aforementioned homogenization step, an aloe mesophyll solution preparation step for recovering, as the aforementioned aloe mesophyll solution, a squeezed liquid obtained by squeezing the aloe mesophyll.

(6) The method for manufacturing an aloe extract according to any one of (1) to (5) which involves carrying out, after the aforementioned enzymatic degradation but before the aforementioned membrane filtration step, a non-volatile component concentration adjusting step for adjusting the concentration of the aloe mesophyll non-volatile components in the enzyme-degraded aloe mesophyll solution.

(7) The method for manufacturing an aloe extract according to any one of (1) to (6) which involves further carrying out a drying step for drying the aforementioned aloe extract which is then recovered as a dried matter.

(8) The method for manufacturing an aloe extract according to (7) which involves carrying out, after the aforementioned drying step, a grinding step for grinding the aforementioned dried matter.

(9) An aloe extract manufactured by a manufacturing method according to any one of (1) to (8).

(10) The aloe extract according to (9) wherein the aforementioned aloe extract contains, based on the solid content of the aloe extract, 2.5 mg/g or more and 7.5 mg/g or less of β-sitosterol and 400 mg/g or more and 900 mg/g or less of dietary fibers.

(11) The aloe extract according to (9) or (10) wherein the median size of the particles contained in the aforementioned aloe extract is 100 μm or less and the 90% particle size is 200 μm or less.

The invention claimed is:

1. A method for manufacturing an aloe extract containing β-sitosterol, phospholipids and dietary fibers comprising the steps of:
    (a) recovering aloe mesophyll from raw leaf of aloe by squeezing liquid from the leaf to produce an aloe mesophyll solution;
    (b) homogenizing the aloe mesophyll solution to produce a homogenized aloe mesophyll solution;
    (c) enzymatically degrading the polysaccharides in the homogenized aloe mesophyll solution with hemicellulase enzyme at a concentration of 0.1 to 1.0% at a temperature between 25° C. to 70° C. for 0.25 to 3.0 hours, to produce a hemicellulase-degraded aloe mesophyll solution;
    (d) filtering the hemicellulase-degraded aloe mesophyll solution with a microfiltration membrane or an ultrafiltration membrane to produce a retentate fraction without polysaccharides with a molecular weight of greater than 10,000 Da; and
    (e) recovering the retentate fraction comprising polysaccharides with a molecular weight of 10,000 Da or less as the aloe extract,
    wherein the aloe extract contains 2.5 to 7.5 mg/g β-sitosterol and 400 to 900 mg/g dietary fibers, based on the solid content of the aloe extract.

2. The method for manufacturing an aloe extract according to claim 1, wherein the homogenized aloe mesophyll solution contains non-volatile components.

3. The method for manufacturing an aloe extract according to claim 1, wherein step (d) is performed with a microfiltration membrane.

4. The method for manufacturing an aloe extract according to claim 1 which involves carrying out, after the hemicellulase degradation but before the membrane filtration step, a non-volatile component concentration adjusting step for adjusting the concentration of the aloe mesophyll non-volatile components in the hemicellulase-degraded aloe mesophyll solution.

5. The method for manufacturing an aloe extract according claim 1 which involves further carrying out a drying step for drying the aloe extract which is then recovered as a dried matter.

6. The method for manufacturing an aloe extract according to claim 5 which involves carrying out, after the drying step, a grinding step for grinding the dried matter.

7. The method for manufacturing an aloe extract according to claim 1, wherein a hemicellulase concentration in the enzymatically degrading step is 0.1%.

8. The method for manufacturing an aloe extract according to claim 1, wherein a hemicellulase concentration in the enzymatically degrading step is 1.0%.

* * * * *